United States Patent [19]

Hanna, Jr. et al.

[11] Patent Number: 5,180,814
[45] Date of Patent: Jan. 19, 1993

[54] TUMOR SPECIFIC MONOCLONAL ANTIBODIES

[75] Inventors: Michael Hanna, Jr., Frederick; Martin V. Haspel, Silver Spring, both of Md.; Herbert C. Hoover, Jr., Port Jefferson, N.Y.

[73] Assignee: Akzo N.V., Arnhem, Netherlands

[21] Appl. No.: 645,069

[22] Filed: Jan. 22, 1991

Related U.S. Application Data

[60] Division of Ser. No. 38,811, Apr. 15, 1987, Pat. No. 4,997,762, which is a division of Ser. No. 697,078, Jan. 31, 1985, which is a continuation-in-part of Ser. No. 575,533, Jan. 31, 1984.

[51] Int. Cl.$^5$ ............................................. C07K 15/28
[52] U.S. Cl. .............................. 530/388.8; 435/240.27
[58] Field of Search ............................. 530/387, 388.8; 435/240.27

[56] References Cited

U.S. PATENT DOCUMENTS 4,997,762 3/1991 Hanna et al. .................. 435/240.27

OTHER PUBLICATIONS

Kohler et al., Nature 256:495-8, Aug. 1975 "Contin. Cultures of fused cells . . . ".

Primary Examiner—Christine M. Nucker
Assistant Examiner—T. Cunningham
Attorney, Agent, or Firm—William M. Blackstone

[57] ABSTRACT

A human monoclonal antibody having specificity for an epitope in a tumor associated antigen, said antibody produced by a cell line selected from the group consisting of Co6a3-1 (HB8493), Co7a4 (HB8494), Co28A32 (HB9380), Co16-86 (HB8496), and Co16-88 (HB8495).

1 Claim, 8 Drawing Sheets

FIG. 2

|  | ANTIBODY | | | | | | | | | |
|---|---|---|---|---|---|---|---|---|---|---|
| PATIENT | 6a3 | 7a2 | 7a4 | 12-38 | 12-42 | 16-4 | 16-58 | 16-66 | 16-88 | 18-21 |
| #1 | ▓ | ▓ | ▓ | ▓ | ▓ | ▓ | ▓ | ▓ | ▓ | ▓ |
| 2 | ▓ |  |  |  |  |  | ▓ |  | ▓ |  |
| 3 | ▓ | ▓ |  |  |  |  | ▓ |  | ▓ |  |
| 4 | ▓ |  | ▓ |  |  | ▓ |  | ▓ | ▓ | ▓ |
| 5 | ▓ | ▓ | ▓ |  |  |  | ▓ |  | ▓ | ▓ |
| 6 |  | ▓ |  |  |  | ▓ | ▓ | ▓ | ▓ | ▓ |
| 7 | ▓ |  |  | ▓ | ▓ | ▓ | ▓ | ▓ | ▓ | ▓ |
| 8 | ▓ | ▓ | ▓ | ▓ | ▓ | ▓ | ▓ | ▓ | ▓ | ▓ |
| 9 |  |  |  | ▓ |  |  |  |  |  |  |
| 10 | ▓ | ▓ |  | ▓ | ▓ |  | ▓ | ▓ | ▓ | ▓ |
| 11 | ▓ | ▓ | ▓ | ▓ | ▓ | ▓ | ▓ | ▓ | ▓ | ▓ |
| 12 | ▓ |  | ▓ | ▓ | ▓ | ▓ | ▓ | ▓ |  | ▓ |
| 13 |  | ▓ | ▓ |  |  |  | ▓ | ▓ | ▓ |  |
| 14 |  | ▓ | ▓ |  | ▓ | ▓ | ▓ | ▓ |  | ▓ |
| 15 | ▓ |  |  | ▓ | ▓ | ▓ | ▓ | ▓ | ▓ | ▓ |

FIG. 3

| PATIENT | 6a3-1 | 7a2 |
|---|---|---|
| #1 | ▓ | ▓ |
| 2 | ▓ | |
| 3 | ▓ | ▓ |
| 4 | ▓ | |
| 5 | ▓ | ▓ |
| 6 | | ▓ |
| 7 | ▓ | |
| 8 | ▓ | ▓ |
| 9 | | |
| 10 | ▓ | |
| 11 | ▓ | ▓ |
| 12 | ▓ | |
| 13 | | ▓ |
| 14 | ▓ | ▓ |
| 15 | ▓ | |
| | (12/15) | (8/15) |
| | (14/15) | |

PARAFFIN SECTIONS

| PATIENT | 6a3-1 | 7a2 |
|---|---|---|
| #17 | ▓ | ▓ |
| 18 | | ▓ |
| 19 | | ▓ |
| 20 | | ▓ |
| 21 | ▓ | ▓ |
| 22 | ▓ | ▓ |
| 23 | ▓ | |
| 24 | | ▓ |
| 25 | | ▓ |
| | (4/9) | (8/9) |
| | (9/9) | |

DISSOCIATED TUMOR CELLS

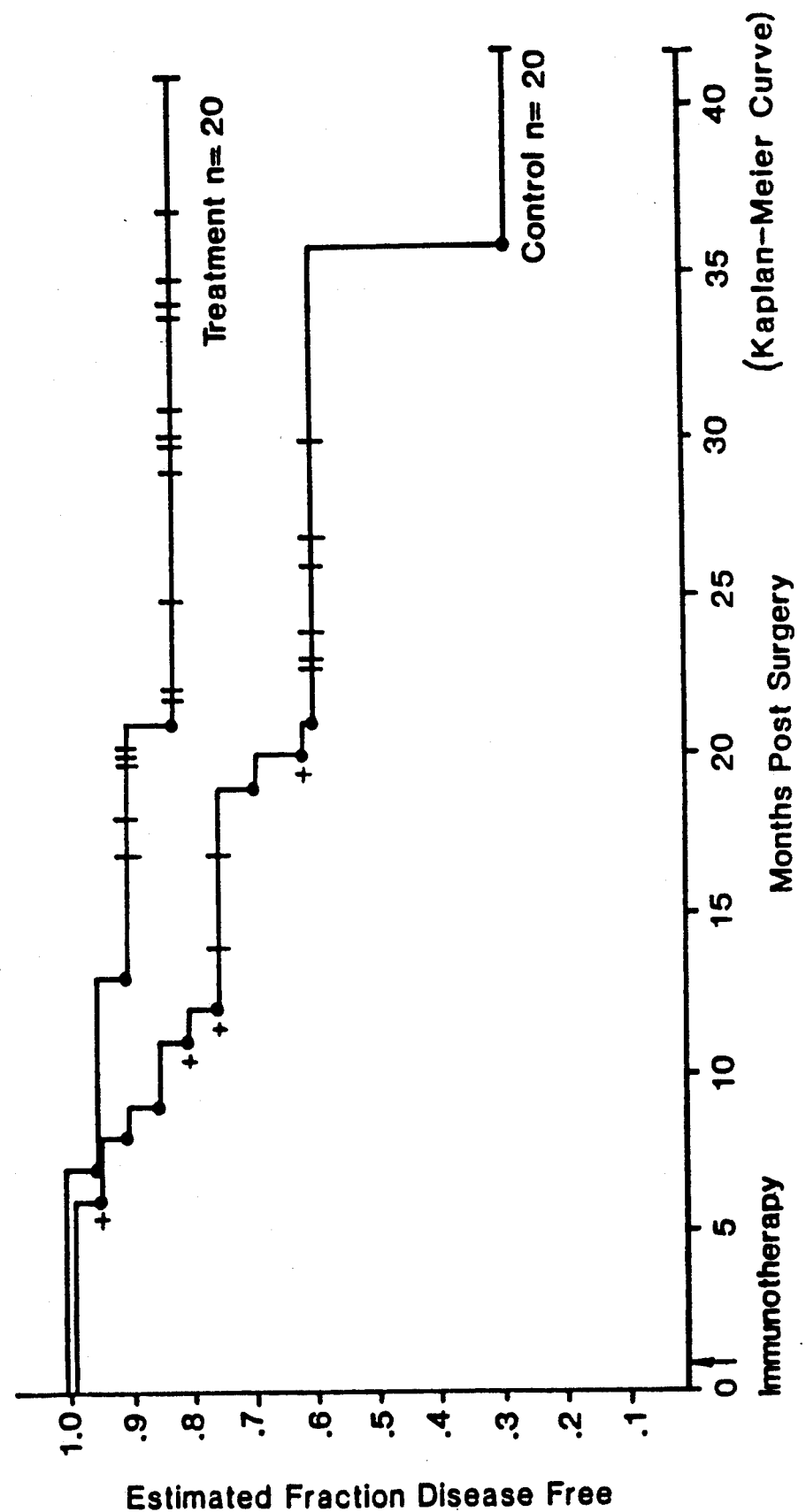

TUMOR SPECIFIC MONOCLONAL ANTIBODIES

This application is a division of application Ser. No. 07/038,811, filed Apr. 15, 1987, issued as U.S. Pat. No. 4,997,762 on Mar. 5, 1991, which is a division of application Ser. No. 06/697,078, filed Jan. 31, 1985, which is a continuation-in-part of U.S. patent application Ser. No. 06/575,533, filed Jan. 31st, 1984.

DESCRIPTION OF THE INVENTION

This invention relates to monoclonal antibodies produced by hybridoma or transformed B-cell lines derived from B-cells of cancer patients actively immunized with autologous tumor antigen. These monoclonal antibodies can be used in both diagnostic procedures and therapy for human cancers. This invention also relates to diagnostic procedures and therapeutic approaches using these monoclonal antibodies.

BACKGROUND OF THE INVENTION

This invention relates to new human monoclonal antibodies which react specifically with antigens associated with particular cancers and to hybridoma and transformed B-cell lines for their production derived from peripheral blood B-cells of actively immunized patients. This invention also relates to methods having general applicability to all solid cancers for preparing hybridomas and monoclonal antibodies and to diagnostic procedures and cancer therapy using these monoclonal antibodies.

Currently available treatments for cancer, particularly radiation therapy and chemotherapy, are based upon the rationale that cancer cells are relatively more sensitive to these treatments than normal cells. However, severe toxicity for normal tissues imposes major limitations to these therapies. In contrast, antibody molecules exhibit exquisite specificity for their antigens. Researchers have therefore sought to isolate antibodies specific for cancer cells as the "long-sought 'magic bullet' for cancer therapy" (*Science*, 1982, 216: 283).

Antibodies are protein molecules normally synthesized by the B-cell lymphocytes produced by bone marrow and carried in the blood stream. For any antigen entering the body, i.e., any foreign molecule from a simple organic chemical to a complex protein, antibodies are produced which recognize and attach to that particular chemical structure. The unique chemical structure on the antigen to which a particular antibody can bind is referred to as an antigenic determinant or epitope. B-cell lymphocytes in the body, referred to as B-cells, lymphocytes, or leukocytes, exist as hundreds of millions of different genetically programmed cells, each producing an antibody specific for a different determinant. An antigen, which stimulates antibody production, can have several determinants on its surface. On encountering an antigen, a B-cell carrying on its surface an antibody specific for a determinant on that antigen will replicate. This clonal expansion results in many daughter cells which secrete that antibody into the blood stream.

Because of the specificity of antibodies in recognizing and binding to antigens, it was desired to produce antibodies in quantity which are specific for a single determinant, thus binding only to antigens or tissues having that particular determinant.

B-cells do not grow in a continuous culture unless they have been altered by hybridization with an "immortal" cell or by being transformed with either viral or tumor DNA. Kohler and Milstein (*Nature*, 1975, 256: 495) demonstrated that hybrid cells could be prepared by somatic cell fusion between lymphocytes and myeloma cells which grow in culture and produce an antibody specific for a single determinant. These hybrids are referred to as "hybridoma cells." Hybridoma cells are prepared by fusing lymphocytes, which have been activated to produce a particular antibody, with myeloma cells. When cultured, hybridomas produce antibodies specific for a single determinant on a particular antigen. Such antibodies are referred to as "monoclonal antibodies."

Monoclonal antibodies may also be produced by B-lymphocyte cell lines that have been spontaneously transformed, either prior to or subsequent to being placed in culture. These cells, in distinction to hybridoma cells, possess a normal human diploid number (46) of chromosomes. This invention permits the isolation of both hybridomas and transformed B-cell lines that produce monoclonal antibodies. For sake of simplicity, both cell types will be referred to as monoclonal antibody producing cells below.

Monoclonal antibodies are synthesized in pure form by a monoclonal antibody producing cell cultures uncontaminated by other immunoglobulins. With such a cell culture, it is possible to produce virtually unlimited quantities of an antibody that is specific for one determinant on a particular antigen.

It has been believed that if antibodies specific for particular cancer cells were available, they could be used in various methods of treatment and diagnosis. Such antibodies could inactivate or kill particular tumor cells merely by attaching to the cell at the determinant for which they are specific. Alternatively, these antibodies may bind to the surface of effector lymphocytes or macrophages, converting them into tumor antigen-specific killer cells.

Monoclonal antibodies can also increase the specificity of chemotherapeutic drugs, toxins and radioactive isotopes, thus increasing their efficacy while decreasing their toxicity. A monoclonal antibody can be conjugated with a toxin, radionuclide or chemotherapeutic drug; this conjugated antibody may be simplistically viewed as a guided missle with the antibody as the guidance system and the drug as the warhead. In addition, antibodies conjugated with radionuclides or metallic tracers can be used for proton emission (PET) and nuclear magnetic resonance (NMR) imaging for in vivo diagnosis and localization of metastases. The antibodies can also be used for detecting the presence of tumor antigens in blood, as a diagnostic and/or prognostic test for cancer. Also, monoclonal antibodies can be used to isolate the tumor antigens for potential use in a standardized vaccine.

The existence of antigens associated with animal tumors was documented in the last century, and the antigenic character of human cancers has been well established, primarily through recent studies with monoclonal antibodies. However, until the research which resulted in this invention, few cancer antigens have actually been characterized in molecular terms and only one group of antigenic determinants associated with human cancers, immunoglobulin idiotypes of B-cell tumors, has been described as being uniquely tumor-specific, i.e., occurring with a high frequency on tumor cells and not occurring to any significant degree on normal tissues (Oldham and Smalley, *J. Biol. Response*

*Modifiers*, 1983; Stratte et al, *J. Biol. Response Modifiers*, Volume 1 1982).

DESCRIPTION OF THE PRIOR ART

Past attempts at deriving monoclonal antibodies specific for human cancers have taken two routes with respect to B-cells: 1) B-cells have been extracted from spleens of mice that were immunized against human tumors, U.S. Pat. No. 4,172,124; and 2) human B-cells have been extracted from either peripheral blood or from lymph nodes draining tumors in cancer patients. Neither approach has yielded satisfactory results.

Mice immunized against human tumors have too broad a reactivity. That is, most of the mouse monoclonal antibodies generated react with human antigens present on normal as well as on tumor tissue. An antibody that reacts only with tumor cells is very difficult to select from among the large variety of antibodies produced. For example, 20,000 hybridomas derived from mice immunized with human small-cell lung carcinoma were screened for reactivity with tumor cells (*Science*, 1982, 216: 283). In contrast to a very low frequency (<0.4%) observed by this research group, the present invention results in up to 16% of the hybridomas derived from immunized colon patients producing monoclonal antibodies that react specifically with tumor cells. In addition, monoclonal antibodies derived from mouse B-cells have limited potential for application in cancer therapy. After repeated administration they tend to stimulate the human immune system to produce "anti-mouse" antibodies which, in clinical trials, have been shown to neutralize the activity of mouse monoclonal antibodies. The use of our human monoclonal antibodies can circumvent these difficulties.

Another apparent difference between human and mouse monoclonal antibodies is their patterns of labeling. Previous studies with mouse antibodies have demonstrated that there is often a heterogenous labeling of cells within tumor sections. This pattern of reactivity has been attributed by some authors to antigenic heterogeneity of tumor cells (Hand et al., *Cancer Research*, 43:728–735, 1983). In contrast, the human monoclonal antibodies developed by our strategy were homogeneous in terms of their reactivity to tumors to which they did react. A plausible explanation for the heterogeneous staining of mouse monoclonal antibodies is that it is a reflection of the murine immune recognition of phase- or cell-cycle-specific differentiation antigens abundant on the tumor cells rather than putative tumor associated antigens. It is not unreasonable to expect that when one immunizes mice with human tumor cells, there would be substantial antigenic competition resulting in the more abundant and more predominant tissue-type and differentiation antigens successfully competing with relatively minor tumor associated antigens for immune responsiveness by the host. Thus, autologous immunization of man may result in the elicitation of antibodies against the group of antigens normally poorly immunogenic in mice. This evidence suggests that humans and mice may respond to different tumor antigens. In concert with this hypothesis is our finding that none of the 36 human monoclonal antibodies we produced appear to react with carcinoembryonic antigen (CEA), an antigen frequently recognized by murine monoclonal antibodies made against human tumor cells.

The majority of past attempts to develop human monoclonal antibodies have used B-cells extracted from either peripheral blood or lymph nodes from patients bearing tumors. It was believed that the presence of the antigenic tumor would cause ta tumor-bearing individual to mount an immune response against his tumor and produce specifically immune B-cells. Thus, B-cells were taken from lymph nodes draining tumors in cancer patients or from circulating lymphocytes found in peripheral blood. However, prior to the present invention, there has been limited success in creating tumor-specific monoclonal antibodies.

The major problem in creating monoclonal antibodies specific for human tumor antigens has been the inability to find a source of specifically immune B-cells (*Science*, 1982, 216: 285). In humans, the initial foci of cancer cells tend to grow over long periods of time, from 1% to 10% of the human lifespan, before there is any palpable clinical evidence of the disease. By this time patients are immunologically hyporesponsive to their tumors, or possibly immunologically tolerant. Thus, prior to the present invention, human monoclonal antibodies reactive with tumor cells could not reproducibly be obtained. Furthermore, of the small number of human monoclonal antibodies obtained from cancer patients, very few reacted with determinants found on the surface of tumor cells, but rather with intracellular determinants (R. J. Cote et al, *PNAS*, 1983, 80: 2026). The present invention permits the development of monoclonal antibodies reactive with surface antigens; a requisite activity for tumor imaging and therapy.

SUMMARY OF THE INVENTION

One object of the present invention was to develop monoclonal antibodies reactive with tumor-specific antigens that induce an immune response in patients having particular cancers. A valid in vivo assay for the immunogenicity of tumor-specific antigens in tumor immunized patients is by delayed cutaneous hypersensitivity. Such antibodies provide a means for detecting and diagnosing tumors. A second objective of this invention was to obtain monoclonal antibodies which would be effective in treating patients with particular types of cancer.

We have developed a new and more effective approach for obtaining monoclonal antibodies by using peripheral blood B-cells from patients immunized with cells from their own tumors in a specific vaccine preparations. To achieve active specific immunotherapy, patients were immunized with autochthonous tumor cells, that is, cells from their own tumors. This approach was taken based on our theory that tumor cells express tumor-specific antigens.

Animal model studies have supported the concept that antigens not found in normal adult tissues are frequently found in tumors, and that the immunogenicity of these tumor cells can be expressed, and even enhanced, in both normal and tumor-bearing hosts. These experimental results validated the rationale of active specific immunotherapy in human neoplasia.

Humans mounting an objective immune response against tumor cells were specifically found to be a good source of activated B-cells. The peripheral blood of patients who had been actively immunized against their own tumors was shown in clinical trials to be an abundant source of such activated B-cells.

It was demonstrated in clinical studies that an objective immune response is generated on treating patients having the particular cancer by skin testing, i.e., delayed cutaneous hypersensitivity (DCH). Immunized patients showed delayed cutaneous hypersensitivity to their own colorectal cancers. In addition, the monoclonal antibodies developed from the immunized patients' B-cells reacted with tumors of the same histological type in other patients. These results indicate that the patient's humoral immune response, production of antibodies, is directed against colorectal cancer generally and is not unique to the immunized patient's own tumor. This general response is especially important for the development of a standardized vaccine.

The treatment also proved to be highly beneficial. Forty-two months after the immunization of the first patients there has been an objective and significant improvement in the patients with respect to duration of the disease-free period following surgery, and the survival data encouraging. Only 3 of 20 treated patients had recurrences and none have died. Comparatively, 9 of 20 patients in a control group had recurrences and four have died.

The generation of B-cells which produce antibodies having reactivity specific for tumor cell antigens, particularly cell surface antigens as in the majority of cases, is an advantageous result that was speculative, at best, when the immunization studies were begun. Only the immunization treatment was observed and measured during the animal studies on which the human immunization procedures were based, not the production of tumor specific antibodies.

The general immune response accompanied by an improvement in the subject's condition was indicative of a cellular response in which macrophages and T-cells become activated in the presence of tumor cell antigens and destroy the tumor cells. Although an antibody response would predictably be triggered by immunization under most circumstances, the time course of the antibody response and the cellular response would in most instances be different. Moreover, the fact that the patients were being immunized with autologous tumor cells, and the experience of previous investigators that little or no antibody production is triggered by a patient's own tumor, made our discovery that B-cells which produce tumor specific antibodies are generated after immunization an unexpected beneficial result.

Some cellular and humoral immune responses can occur independently of each other. For example, it is possible to mount a humoral response in the absence of demonstrable cellular immunity. Conversely, potent cellular immunity, particularly delayed cutaneous hypersensitivity (DCH), may develop despite a minimal antibody response. It was surprising, therefore, for the subjects who showed a positive response to active immunotherapy to have been excellent sources of B-cells producing tumor specific antibodies, particularly cell surface antibodies.

A third objective of this invention was to prepare a standardized vaccine for use in detecting and treating specific cancers in the general population which did not require the custom preparation of a new immunogen suitable for each individual patient. Without a standardized vaccine, only a vaccine prepared for each individual patient from his own tumor tissue could be used for therapy, and only known cancers could have been treated on a limited scale in large institutions. It would not have been possible to make individual preparations for treating the approximately 139,000 cases of colorectal cancer that are discovered in the United States every year.

This invention comprises the preparation of successful vaccines for active specific immunization, procedures for extracting immunized B-cells, the production of monoclonal antibody producing cells and the production of monoclonal antibodies. Malignant tumors are digested using enzyme preparations. The cells obtained are treated to yield a non-tumorigenic tumor cell preparation having the requisite cell viability, which is injected as a vaccine into the subject from which the tumor was obtained. Peripheral blood B-cells are obtained from the inoculated subject after a predetermined interval and are used to prepare monoclonal antibody producing cells by fusing with myeloma cells, after which the fused cells are screened for the synthesis of immunoglobulin. Cells that synthesize immunoglobulin are tested for production of antibodies which react with antigens characteristic of the malignant tissue. Those selected are cultured to produce monoclonal antibodies that react with the particular type of tumor with which the subject was afflicted.

Mouse myeloma cells grown in culture were used to prepare hybridomas in the research which led to this invention. However, as the problems with developing easy-to-grow human myeloma cell lines that do not produce antibodies of their own are solved, human myelomas will be preferred for preparing the hybridomas of this invention.

DETAILED DESCRIPTION OF THE INVENTION

The key aspects of this invention are:

1) Criteria for successful vaccines for active specific immunization:

Tumor cells, whole cells enzymatically dissociated from tissue, cryopreserved and X-irradiated for non-tumorigenicity.

Adjuvant, an immunomodulator that is capable of inducing immunogenecity to the tumor cell preparation.

Components and administration, including ratio of adjuvant to tumor cells, optimum doses of tumor cells, and regimen of vaccination.

Patient, regional lymph nodes draining the vaccination site must be present during the first 21 days after vaccination.

2) Procedures and timing for the extraction of immunized B-cells from the patients.

3) Procedures for the production of hybridomas and transformed lymphocytes and production of monoclonal antibodies.

We have successfully digested solid human malignancies using various enzyme preparations. The tumor dissociations were evaluated for yield of tumor cells per gram of tissue, cell types recovered, cell viability, cell size, and sterility. The criteria for successful vaccines for active specific therapy are shown in Table 1.

Tumor tissue was obtained from patients suffering from the particular solid cancer for which monoclonal antibodies were to be prepared. The tumor tissue was surgically removed from the patient, separated from any non-tumor tissue, and cut into small pieces. We found it satisfactory to cut the tumor tissue into fragments 2-3 mm in diameter. The tumor fragments were then digested to free individual tumor cells by incubation in an enzyme solution.

After digestion, the freed cells were pooled and counted, and cell viability was assessed. The trypan blue exclusion test was found to be an acceptable measure of cell viability. The tumor cells were then cryopreserved and stored in liquid nitrogen.

The vaccine was prepared for injection by rapidly thawing cryopreserved cells, diluting the cells, washing with HBSS, resuspending, counting, and assessing viability.

Viable tumor cells were irradiated to render them non-tumorigenic. We found that irradiation with 4020 rads/min for a total of 20,000 rads resulted in non-tumorigenic but viable cells. The volume of the cell suspension in HBSS was adjusted such that $10^7$ viable cells remained in the tube. The cells were centrifuged, the supernatant was removed, and $10^7$ viable BCG were added in a volume of 0.1 ml. Hank's Balanced Salt Solution (HBSS) was added in sufficient quantity for a final volume of 0.2 ml. A third vaccine was similarly prepared, omitting the BCG.

Immunization of Patients

Patients afflicted with the particular solid cancer for which antibodies were to be generated were immunized by intradermal inoculation with the tumor cell vaccine. $10^7$ viable tumor cells admixed with BCG were used for the first two vaccinations and $10^7$ tumor cells alone were used for the third vaccination. Scheduling each vaccination one week apart was found to be a successful procedure for inducing antibody production by the patients' peripheral blood lymphocytes.

Collection of Immunized B-Cells

Venous blood was collected from the immunized patients one week after each vaccination. Peripheral blood lymphocytes (PBL) were separated from the collected blood for use in hybridoma production.

Separation of lymphocytes from the blood was accomplished using two different methods. The first comprised dilution with calcium and magnesium-free HBSS, layering on lymphocyte separation medium, centrifuging, and removing cells at the interface. These cells were diluted with HBSS and pelleted. The lymphocytes were then resuspended in serum-free Hepes-buffered Dulbecco's MEM (DMEM), counted, and assayed for viability (GIBCO Biologics, Grand Island, N.Y.).

An alternative method that was used to recover peripheral blood lymphocytes (PBLs) enriched for B-cells comprised the removal of T-lymphocytes by rosetting with 2-aminoethylisothiouronium bromide hydrobromide (AET) treated sheep erythrocytes. Treated erythrocytes were mixed with peripheral blood lymphocytes, pelleted by centrifugation, and the pellet incubated on ice. After resuspension, layering over lymphocyte separation medium (LSM, Litton Bionetics), and centrifugation of the rosetted cells, the T-cell depleted PBLs were collected at the interface, washed, and pelleted. The PBLs enriched for B-cells were then used for hybridoma generation after counting and viability determination.

Preparation of Human Hybridomas for the Production of Anti-Tumor Monoclonal Antibodies Peripheral blood lymphocytes (PBLs) and cultured myeloma cells were mixed together, pelleted, and resuspended in a serum-free medium. Polyethylene glycol (PEG) was added, the cells pelleted and resuspended in HT medium (DMEM containing 20% fetal bovine serum, hypoxanthine and thymidine) and distributed into microtiter wells. Twenty-four hours later, HAT medium (HT medium containing aminopterin) was added to each well, with one-half of the medium being replaced every three days. After maintenance in HAT medium for 14 days, the cells were maintained on HT medium for an additional two weeks, after which the cells were grown on a DMEM medium containing 20% fetal bovine serum.

The hybridomas were pre-screened for the synthesis of human immunoglobulin using the standard enzyme immunoassay. Hybridomas synthesizing human immunoglobulin in sufficient amounts were tested on tissues. Particular tissue samples were incubated with hybridoma supernatant fluids. Supernatants which demonstrated reactivity with particular tumor tissues indicated that hybridoma cells in the wells from which the particular supernatants were drawn produced tumor-specific antibodies. If the same supernatants failed to show a reaction with samples of normal tissue after extensive screenings, the hybridomas in that particular well were considered tumor-specific. These tumor-specific supernatants were further tested against carcinoembryonic antigen (CEA) to be sure of their narrow specificity.

In addition to hybridoma cells which produced tumor-specific antibodies, transformed human B-cells (diploid cells) were also prepared by these procedures which also produced tumor-specific antibodies. The transformed B-cells were detected in the same way as tumor-specific antibody-producing hybridomas. Thus, well supernatants which tested positively for reactions with tumor tissue and negatively for reactions with normal tissue and with CEA contained either hybridomas or transformed B-cells. The two types of cells were differentiated by observing that the transformed B-cells contained 46 human chromosomes, whereas the hybridomas contained many more chromosomes, not all of which were of the human type.

The mechanism by which B-cells become transformed during the above described prcedures has not been precisely determined.

with affinity-purified peroxidas-labeled goat antibody to human immunoglobulins (IgG+IgA+IgM), washed and then reacted (15 min. at room temperature) with diaminobenzidine (0.5 mg/ml) in PBS (pH 7.6) containing 0.1% $H_2O_2$. After counterstaining with hematoxylin, the section was dehydrated, cleared and mounted with permount.

Figure 1A:
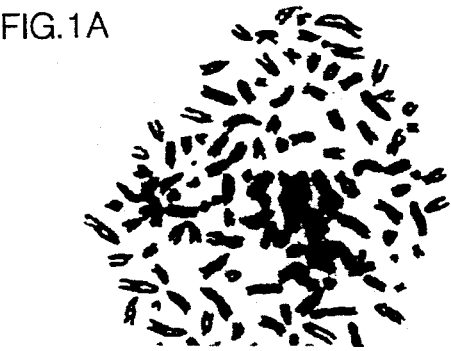
FIG. 1A: Chromosome spread of a cell with growth characteristics typical of hybridomas ($\times 1600$). LiCo 21B27 was incubated with colcemid (0.05 μg/ml) for two hours and treated with hypertonic (0.075M) KCl for three minutes. The cells were fixed with methanol-acetic acid (3:1), dropped onto microscope slides, air-dried and stained with Giemsa. Both human and mouse chromosomes are present.
Figure 1B:
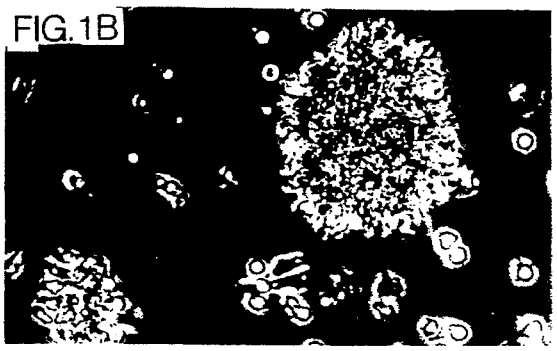
FIG. 1B: Phase photomicrograph of a clusterforming monoclonal antibody (LiCo 18-15) producing cell line ($\times 270$). Note the aggregation and irregular shape of the cells.
Figure 1C:
FIG. 1C: G-banded chromosome spread of the cell line shown in FIG. 1D ($\times 1360$). Note the absence of mouse chromosomes. The cells were incubated with colcemid (0.01 μg/ml) overnight. The chromosome spreads were prepared as described above. The unstained slide was aged for 10 days. The chromosomes were treated with trypsin (0.19% for 30 seconds at room temperature), dehydrated with ethanol and stained with Giemsa.
Figure 1D:
FIG. 1D: Formalin-fixed (10%) paraffin-embedded section of a colon carcinoma reacted with LiCo 16-88 · (4 μg/ml IgM $\times 380$). Both surface-like and cytoplasmic labeling are seen. The deparaffinized section was blocked (20 min. at room temperature) with phosphate-buffered saline (PBS) (pH 7.3) containing 0.75M L-lysine and 1% bovine serum albumin and then incubated with LiCo 16-88 overnight at 4° C. After washing with PBS the section was incubated (60 min. at 37° C.)
Figure 1E:

FIG. 1E: Colon tumor as in FIG. 1D, reacted with normal human IgM (4 μg/ml) (×380). No staining is observed.

Figure 1F:

FIG. 1F: Cryostat section of a colon tumor stained by LiCo 16-88 (×640). Note the intense label of the periphery of the tumor cells (arrows). The section was air dried and stored at −30° C. This section was post-fixed (20 min. at 4° C.) with PLP in PBS and processed as described in FIG. 1D, except that peroxidase-labeled goat antibody specific to human μ chains was used.

Figure 1G:
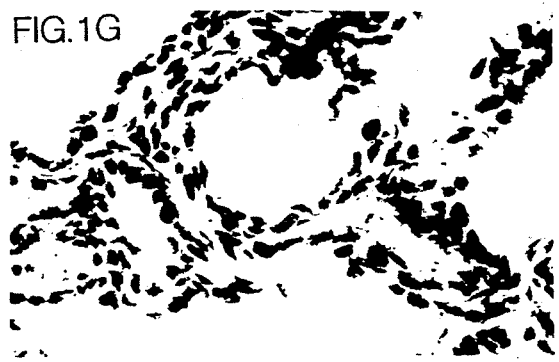

FIG. 1G: Cryostat sections of the colon tumor seen in FIG. 1F reacted with normal human immunoglobulin (×640). No labeling of the tumor cells is seen.

Figure 1H:
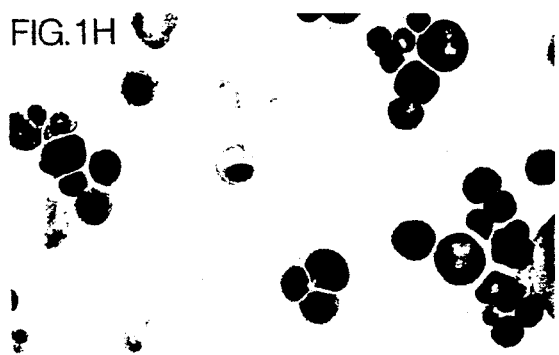

FIG. 1H: Cytospin preparation of air-dried unfixed SW1463 cells stained by LiCo 16-88 (4 μg/ml) (×280). The colon tumor cell line was harvested with ethylenediaminetetraacetic acid (EDTA) (0.02%), washed and suspended in medium containing 1% bovine serum albumin. Cells ($2 \times 10^4$ in 0.1 ml) were pelleted onto the glass slides in a cytocentrifuge, air dried and stored at −30° C. Cells were incubated with monoclonal antibody (1 hr. at room temperature and then overnight at 4° C.), washed and then processed as described above.

FIG. 2: Distribution of antigens in paraffin sections of colorectal tumors. Shaded area indicates positive indirect immunoperoxidase staining of 15 tumors by 10 human monoclonal antibodies.

FIG. 3: Two monoclonal antibodies react with most colorectal tumors. The reactivity of two monoclonal antibodies to paraffin sections of 15 colorectal tumors and air-dried cytospin preparations of dissociated tumors from 9 patients are compared. Shaded area indicates positive indirect immunoperoxidase staining.

Figure 4:
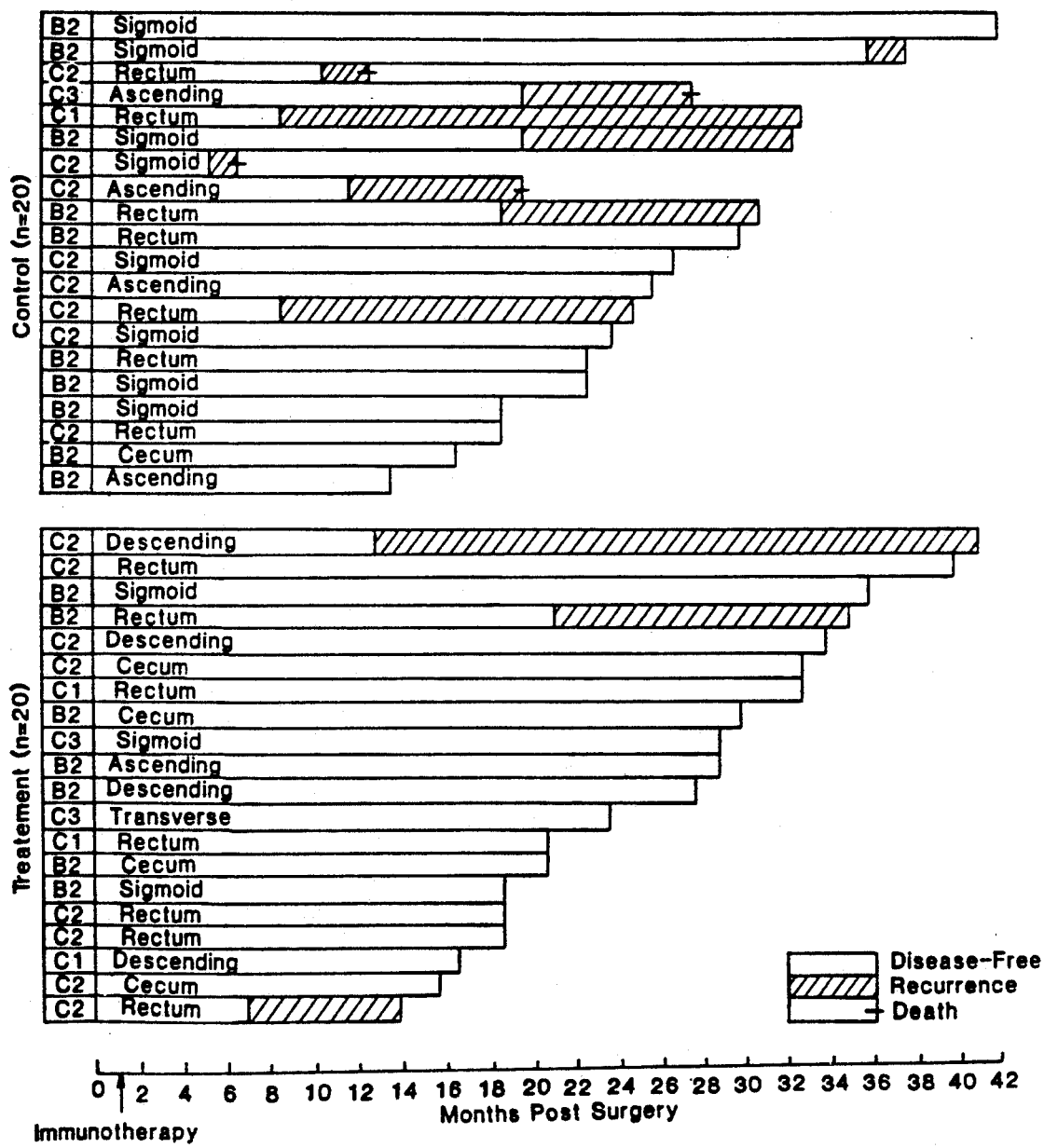

FIG. 4: Follow-up of all control and immunized patients in active specific immunotherapy clinical trials according to site and pathologic stage.

FIG. 5A: Disease-free status of all patients.

Figure 5B:
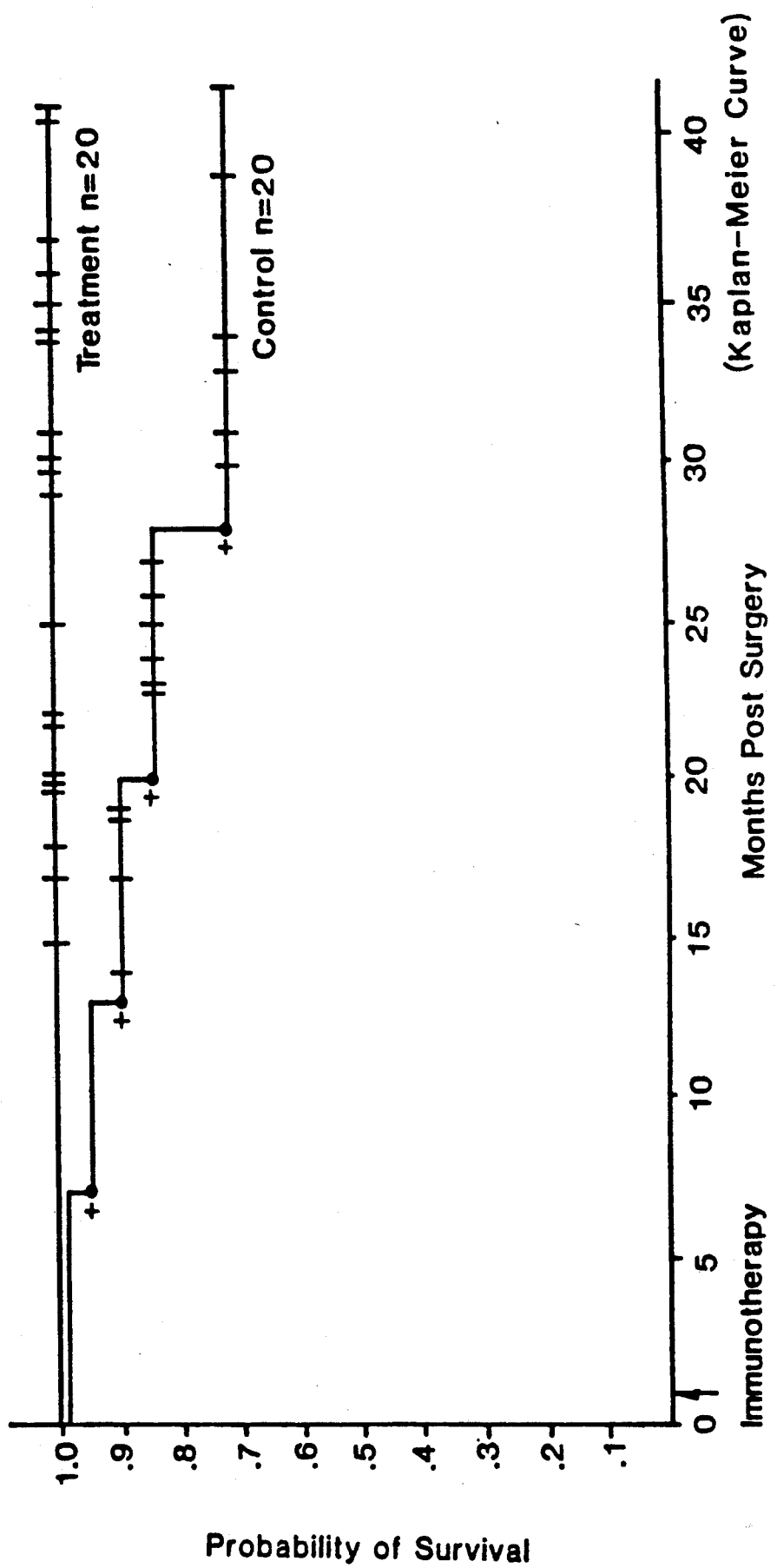

FIG. 5B: Survival status of all patients.

Figure 6A:
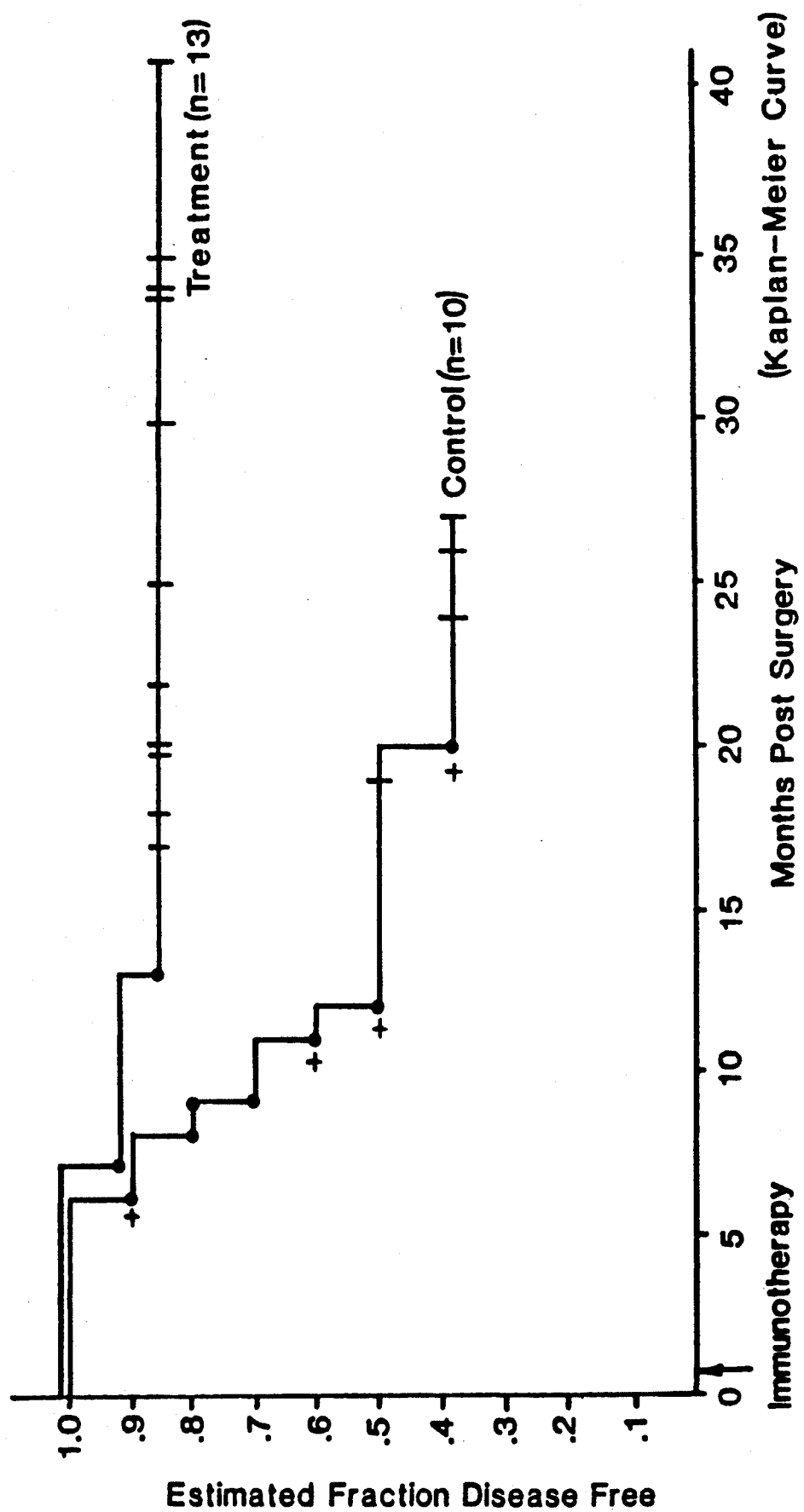

FIG. 6A: Disease-free status of patients with positive regional lymph nodes (Astler-Coller C).

Figure 6B:
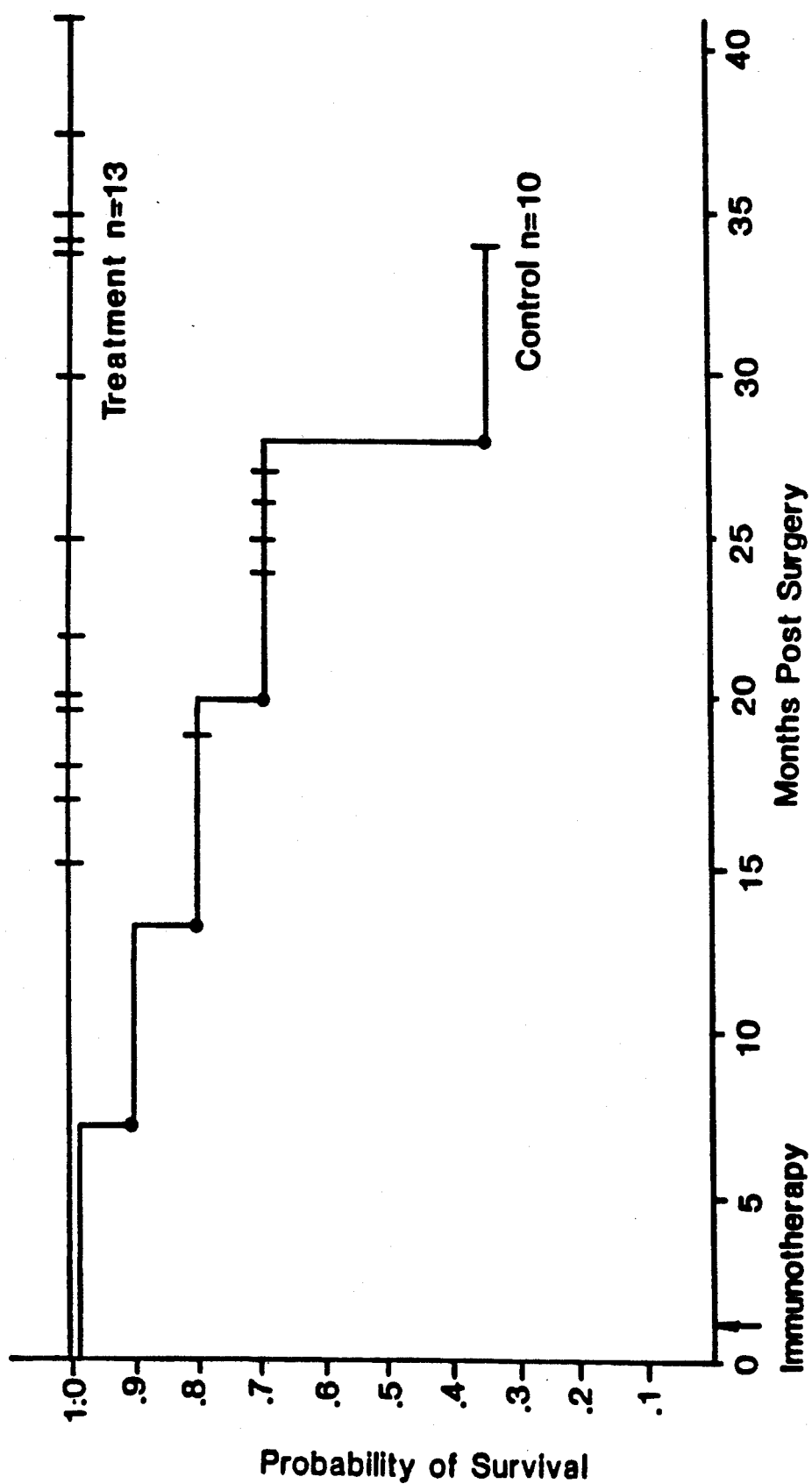

FIG. 6B: Survival status of patients with positive regional lymph nodes (Astler-Coller C).

EXAMPLE I

PREPARATION OF SENSITIZED B-CELLS

A. Patient Selection.

Patients undergoing surgical resection of colon or rectal cancers were selected for a randomized trial of active-specific immunotherapy. Randomization was done with stratification according to pathologic stage and tumor was obtained from all patients who met the clinical criteria. Candidates for the study were colorectal cancer patients with no previous history of cancer, who had received no prior chemotherapy or radiation therapy, and who were in suitable medical condition to comply with the outpatient treatment protocol. Patients eligible for the trial were those with tumor extending through the bowel wall (Astler-Coller B2), positive lymph nodes (stages C1, C2) or patients with metastatic disease (stage D). Within these classifications, patients were randomly selected for participation in treatment and nontreatment groups. Randomization cards were computer generated and sequentially drawn from each category postoperatively.

B. Tumor Acquisition.

After surgical resection the bowel specimen was taken immediately to the hospital pathology department and opened under sterile conditions. Tumor tissue was excised, placed in sterile tubes containing Hank's Balanced Salt Solution (HBSS) containing 50 μg gentamicin per ml and carried immediately on ice to the laboratory for processing and freezing.

C. Dissociation of Solid Tumor and Colon Mucosa.

The tissue dissociation procedure of Peters et al (*Cancer Research*, 39:1353–1360, 1979) was employed using sterile techniques throughout under a laminar flow hood. Tumor tissue was rinsed three times in the centrifuge tube with HBSS and gentamicin and transferred to a petri dish on ice. Scalpel dissection removed extraneous tissue and the tumor was minced into pieces approximately 2 to 3 mm in diameter. Tissue fragments were placed in a 75 ml flask with 20–40 ml of 0.14% (200 units/ml) Collagenase Type 1 (Sigma C-0130) and 0.1% (500 Kunitz units/ml) deoxyribonuclease type 1 (Sigma D-0876) (DNAase 1, Sigma D-0876) prewarmed to 37° C. Flasks were placed in a 37° C. waterbath with submersible magnetic stirrers at a speed which caused tumbling, but not foaming. After a 30-minute incubation, free cells were decanted through three layers of sterile medium-wet nylon mesh (166 t: Martin Supply Co., Baltimore, Md.) into a 50 ml centrifuge tube. The cells were centrifuged at 1200 rpm (250×g) in a refrigerated centrifuge for 10 minutes. The supernatant was poured off and the cells were resuspended in 5–10 ml of DNAase (0.1% in HBSS) and held at 37° C. for 5–10 minutes. The tube was filled with HBSS, washed by centrifugation, resuspended to 15 ml in HBSS and held on ice. The procedure was repeated until sufficient cells were obtained, usually three times for tumor cells. Cells from the different digests were then pooled, counted, and cell viability assessed by the trypan blue exclusion test. The cells were centrifuged for a final wash prior to cryopreservation.

D. Cryopreservation.

Optimal cryopreservation was a primary concern. For vaccine preparation, the dissociated tumor cells were adjusted to $5-8 \times 10^7$/ml in HBSS and added in equal volume to chilled 2×freezing medium containing 15% dimethylsulfoxide (DMSO) and 4% human serum albumin (HSA). The final suspension of 2 to $4 \times 10^7$ cells/ml were placed in 1.2 ml Nunc freezer vials. For DCH cell testing the procedure was the same except that no HSA was used. In both cases, in preparation for freezing, the Nunc vials were transferred on ice to a Cryo-Med model 990 Biological Freezer with a model 700 Controller and a model 500 Temperature Recorder for controlled-rate freezing. Care was taken that the temperature of the individual vials, including the monitor vial, was uniform at the beginning of the freezing process. Vials were cooled at a controlled rate of −1° C./min to a final temperature of −80° C. The vials were transferred in liquid nitrogen to liquid nitrogen storage.

E. Clinical Protocol.

Patients with tumors of the appropriate pathologic stages were randomized to receive either the autologous tumor cell-BCG vaccine or to have no further therapy. The stage D patients all received 5-fluorouracil chemotherapy and all patients with lesions below the peritoneal reflection (rectal cancer) received 5040 rads of pelvic X-irradiation two weeks after immunotherapy was completed. The vaccines were started at 4-5 weeks after tumor resection to allow sufficient time for recovery of immunologic suppression induced by anesthesia and surgery. At 3-4 weeks after resection, both control and treatment patients were skin tested with standard recall antigens as well as graded doses of their autologous tumor cells. Recall antigens used were: Mumps skin test antigen, USP, Eli Lilly, Indianapolis, Ind.; Aplisol, PPD, (Tuberculin Purified Protein Derivative), Parke-Davis, Detroit, Mich., Trichophyton, diluted 1:30, Center Laboratories, Port Washington, N.Y.; and Candida albicans diluted 1:100, Center Laboratories, Port Washington, N.Y., 0.1 ml of each was placed intradermally on the forearm and examined for erythema and induration at 24 and 48 hours.

Patents selected for treatment protocol received 3 weekly intradermal vaccine injections consisting of $10^7$ irradiated, autologous tumor cells and $10^7$ BCG in the first 2 vaccines with $10^7$ tumor cells alone in the final. Fresh-frozen Tice BCG, supplied by Dr. Ray Crispen, University of Illinois Medical Center, Chicago, Ill., was stored at $-70°$ C. The first vaccine was placed on the left anterior thigh approximately 10 cm below the groin crease, the second in a comparable location on the right thigh and the third in the right deltoid area.

F. Preparation of Vaccine.

On the day of the first and second vaccinations, the vial was rapidly thawed in a 37° C. waterbath, tumor cells were diluted slowly to 15 ml in HBSS, washed once by centrifugation at 1200 rpm and resuspended to 15 ml in HBSS. Cell counts and viability determinations were made using the trypan blue exclusion test. Viability ranged between 70 and 90%, with a mean of 80%. The cells were washed once by centrifugation at 1200 rpm and resuspended to 15 ml in HBSS. The suspension of tumor cells was placed on ice and irradiated at 4020 rads/min for a total of 20,000 rads. The volume of the cell suspension was adjusted such that $10^7$ viable tumor cells remained in the tube ($1.3 \times 10^7$ viable cells are included to allow for cell loss in tubes and syringes, and for the possibility of approximately 20% misidentification of lymphoid cells). The cells were centrifuged, the supernatant removed and $10^7$ BCG were added in a volume of 0.1 ml. HBSS was added in sufficient quantity for a final volume of 0.2 ml. The third vaccine was similarly prepared, omitting the BCG.

The vaccine suspension was drawn up through a 20 gauge needle into a 1.0 ml tuberculin syringe. The 20 gauge needle was replaced with a 27 gauge needle for the intradermal injection, and the syringe was placed on ice for transport to the clinic.

The patients were observed closely after each vaccine for erytherma and induration at the site of injections, fever, lymphadenopathy or any adverse reactions. The first two vaccine sites ulcerated after 2-3 weeks but always healed within 10 to 12 weeks.

G. Results of Immunization.

Reactivity to Standard Recall Antigens

All patients were reactive initially to at least one of the standard recall antigens. Two of the 29 were reactive to candida, 26 of 29 were reactive to mumps, 16 of 29 were reactive to PPD and 3 of 29 reacted to trichophyton. There was no significant change in reactivity in the followup period except that all but two of the immunized patents converted to PPD positivity.

H. Delayed Cutaneous Hypersensitivity (DCH) to Tumor Cells

The delayed cutaneous hypersensitivity reaction to $10^6$ autologous tumor cells in 24 immunized and 11 nonimmunized control patients is shown in Table 2. A 48-hour induration measurement of greater than 5 mm was considered positive. Four of 24 patients (17%) had a positive DCH to $10^6$ tumor cells prior to the course of immunization. This was not significantly different from the one of 11 patients (9%) testing positive in the nonimmunized control group. Of significance ($p<0.01$) all of the initially four positive responders and 12 of the negative responders in the immunization group boosted to greater DCH reactivity following a course of immunotherapy (67% became positive). Seven of these patients have been tested at one year, with three maintaining a positive response. Only three of the 16 objectively immunized patients demonstrated a positive DCH response to $10^5$ tumor cells at 6 weeks, with none showing a response to $10^4$ cells.

EXAMPLE II

PRODUCTION OF HYBRIDOMAS FOR HUMAN MONOCLONAL ANTIBODIES

A. Removal and Processing of Immunized B-Cells from Patients

Patients were bled at the time of the second immunization, one week after the first immunization, and at the time of the third vaccination, one week after the second immunization. Venous blood was collected asceptically in the presence of preservative-free heparin (O'Neill, Jones and Feldman, St. Louis, Mo.) at a final concentration of 17 units/ml. The blood was maintained at room temperature and transported to the laboratory expeditiously, within a few hours of collection.

The blood, diluted 1:2 with calcium and magnesium-free HBSS, was layered (4 ml) over 3 ml of lymphocyte separation medium (LSM, Litton Bionetics) and centrifuged in a 15 ml centrifuge tube for 30 minutes at $400 \times g$. The cells at the interface were removed, diluted with three times their volume of HBSS and pelleted (1000 rpm for 10 minutes). The peripheral blood lymphocytes (PBL) were resuspended in 10 ml of serum free Hepes buffered Dulbecco's MEM (DMEM), counted and viability determined.

An alternative method was also used to recover immunized B-cells. The T-lymphocytes were removed by rosetting with AET-treated sheep erythrocytes. Sheep erythrocytes (in Alsever's solution) were washed three time with balanced salt solution (BSS) and incubated at 37° C. for 20 minutes with four times the packed cell volume with 0.14M AET (Sigma). The treated cells were then washed three times with HBSS and resuspended to a 10% suspension. The treated erythrocytes were layered over LSM, centrifuged at 2500 rpm and the pellet collected. Following three washes with HBSS, the sheep erythrocytes were resuspended to a 10% suspension in undiluted fetal bovine serum and used within two weeks. The PBL (up to 80 million cells) were mixed with 1 ml of AET-treated sheep erythrocytes and pelleted at 1000 rpm for 10 minutes at 4° C. The pellet was incubated on ice for 45 minutes, gently resuspended with a wide bore pipette and layered over 3 ml LSM. The rosetted cells were centrifuged at $400 \times g$ for 40 minutes at room temperature. The T-cell depleted PBLs were collected at the interface, washed with three times the volume HBSS, and pelleted. Following counting and viability determination, the PBLs enriched for B-cells were then used for hybridoma generation.

B. Generation of Human Hybridomas.

Mouse myeloma cells (NS-1) were grown in the presence of 8-azaguanine (20 μg/ml). Three days before fusion, the cells were pelleted and passaged in medium free of 8-azaguanine. The cells were passaged again the day before fusion to maintain them in log phase. The myeloma cells were washed once with serum-free medium, counted, and viability determined. The PBL and myeloma cells were mixed at a ratio of 3:1 and pelleted together at 1000 rpm for 10 minutes. All supernatant fluid was removed and the cell pellet resuspended in less than 100 μl of serum-free medium. One ml of polyethylene glycol (50% w/v) prewarmed to 37° C. was added dropwise to the cell pellet over the course of one minute with constant agitation of the tube. Twice the previous volume of pre-warmed serum-free medium was added to the cell suspension over the course of one minute until the 50 ml tube was filled. The cells were pelleted at 800 rpm for 15 minutes. The cells were gently resuspended in HT medium (DMEM containing 20% fetal bovine serum, hypoxanthine 13.6 μg/ml and thymidine 3.9 μg/ml) at a concentration of $2.5 \times 10^6$ cells/ml (pre-fusion count) and 100 μl was added to each microtiter well. Twenty-four hours later, 100 μl of HAT medium (HT medium containing 0.18 μg/ml aminopterin) was added to each well. Half of the medium was replaced every three days with fresh HAT medium. After maintenance in HAT medium for 14 days, the cells were maintained on HT medium for an additional two weeks, at which time the cells were grown on a DMEM medium containing 20% fetal bovine serum.

Alternatively, co-cultivation of PBL with myeloma cells may be used to generate transformed diploid B-cells. PBL and myeloma cells were mixed (at a ratio of 3:1), pelleted at 800 rpm and selected in HAT medium, as described above.

C. Screening of Hybridomas.

The hybridomas were first quantified and isotyped by a capture enzyme-linked immunoassay (ELISA) for the synthesis of human immunoglobulin (IgA, IgG and IgM). The standard Bio-EnzaBead method was utilized, which is sensitive in the range of 10-300 ng/ml. The hybridoma supernatant fluids were diluted 1:30 with an effective range of 0.3-9 μg/ml. Only hybridomas that synthesized human immunoglobulin at a concentration of greater than or equal to 1 μg/ml were tested by indirect immunoperoxidase on tissues after the isotype of the antibody (IgA, IgG or IgM) was determined.

Polycarbonate-coated metallic beads (Bio-EnzaBead ™, Litton Bionetics) were incubated with goat antibodies to human immunoglobulins (IgG+IgA+IgM) overnight at 4° C. and then blocked (30 min at room temperature) with 2.5% BSA to prevent non-specific binding. The beads were then air dried and stored at 4° C. The ELISA for detection of immunoglobulin was performed as follows. Supernatant fluid from a 96-well culture plate was diluted, incubated with the antibody-capture bead for 1 hr at 37° C., washed, and then incubated for 1 hr at 37° C. with peroxidase-labeled affinity-purified goat antibody to human immunoglobulins (IgG+IgA+IgM). The washed beads were then incubated (10 min at room temperature) with 2,2'-Azino-di[3-ethyl-benzthiazoline-6-sulfonic acid], and the optical density was determined at 405 nm. The immunoglobulin concentrations were interpolated mathematically from the linear portion of a standard curve (30-1000 ng/ml) of human gamma globulin. Supernatant fluids containing >1 μg/ml were then isotyped using this ELISA with peroxidase-labeled goat antibodies to human γ, α, and μ chains. Subsequent quantitative assays used an immunoglobulin standard appropriate for the monoclonal antibody isotype. Mouse immunoglobulins were assayed with Bio-Enza-Beads coated with goat antimouse IgG+IgM (H+L) and peroxidase-conjugated goat antimouse IgG+IgM (H+L). In other experiments, supernatant fluids were incubated with the antihuman Ig beads and the peroxidase-conjugated goat antimouse IgG+IgM (H+L).

Cryostat sections of normal and tumor tissue, stored at −30° C., were post-fixed in PLP (0.5% p-formaldehyde, 0.075M L-lysine, 0.01M sodium periodate) for 20 minutes at 4° C. The sections were then washed. Paraffin sections of 10% formalin-fixed tissues were deparaffinized immediately before use. The cryostat and paraffin sections were then incubated at room temperature in 1% bovine serum albumin in PBS containing 0.075M L-lysine for 20 minutes. The sections were incubated overnight at 4° C. with hybridoma supernatant fluids. Following three washes with PBS, the sections were then incubated with the appropriate anti-human peroxidase-labeled reagent for 60 minutes at 37° C., washed and incubated at room temperature for 15 minutes with diaminobenzidine (0.5 mg/ml, pH 7.6) in PBS containing 0.1% hydrogen peroxide. The sections were washed with PBS, stained with hematoxyline, dehydrated, and mounted with permount.

These methods permitted the widest spectrum of tissue reactive antibodies to be detected (i.e., directed against surface or cytoplasmic antigens).

To isolate broadly reactive antibodies, the supernatant fluids were screened against a panel of tumor sections. Cell lines producing monoclonal antibodies were then cloned by limiting dilution. Twenty-two fusions were performed with peripheral blood lymphocytes obtained from ten patients, and two fusions were done with lymphocytes from patients before immunization. Optimal results were obtained with lymphocytes removed one week after the second immunzation (Table 8). The frequency of immunoglobulin producing clones isolated after the second immunization was almost twice that after the first immunization. Seven of the 36 tissue-positive monoclonal antibodies reacted with cryostat sections but not with paraffin embedded tissues. This finding underscores the need for broad screening procedures. More than two-thirds of the clones produced IgM, most probably a consequence of the source of the lymphocytes (peripheral blood).

One-third of the cell lines had morphology typical of hybridomas and grew as dispersed cells. Karyotypic analysis of six representative hybrids demonstrated that they were human-mouse hetero-hybridomas (FIG. 1A). By contrast, the majority of the monoclonal antibody synthesizing cell lines (24 out of 36) were atypical in appearance (FIG. 1B). These cells were predominantly irregular in shape and grew in large aggregates. These cluster-forming cells were isolated in seven fusions performed with PEL from seven of ten colon patients. Thus, they appear to be quite common. Six cell lines representing five fusions from four patients, were karyotyped and were found to contain 46 chromosomes. G-banding of the chromosomes confirmed that they were of human origin (FIG. 1C). Thus, based upon the criterion of cell morphology, it appears that the majority of the monoclonal antibody-synthesizing cell lines are not hybridomas but rather are transformed human B-cells (diploid cells). The mechanism of this spontaneous transformation is not known but may be related to the immunization procedure.

No clear differences exist between these cell types in the isotype of secreted immunoglobulin or the type of tissue stained. The amounts of immunoglobulin (1-60 µg/ml) secreted by both cell types were essentially comparable, with most of the human cells producing 5-60 µg/ml. As may be expected, the diploid cells appear to be more stable with regard to immunoglobulin production. These cells were grown in continuous culture for up to 9 months without any indication of a finite life span for antibody production. In fact, increases in antibody production during long-term culture were observed for some diploid lines. The clones which subsequently became non-producers during extensive cell passage had growth properties typical of hybridomas. However, most hybrids had sufficient stability to permit the production of useful quantities of antibody. For example, human-mouse heterohybridoma 7a2 was passaged for more than 20 generations from a recently cloned seed stock of $5 \times 10^6$ cells without a decrease in antibody production. Thus, the cells theoretically could be expanded to $7 \times 10^{13}$ cells. This hybrid produced approximately 30 µg/ml/$10^6$ cells and thus $7 \times 10^{13}$ cells could conceivably produce over 2 kg of antibody.

D. Production of Monoclonal Antibodies.

Human monoclonal antibody producing cells were grown in RPMI 1640 medium (Gibco, Grand Island, N.Y.) supplemented with 10% fetal bovine serum, 3 mM L-glutamine and 5 µg/ml gentamicin. The medium was in some cases further supplemented with 25% D-glucose (final concentration 0.25%). The cells were at 37° C. (35°-38° C.) under a humidified atmosphere of 7.5% $CO_2$ in air. The antibody was harvested from the highly metabolized spent medium by pelletizing the medium free of cells (e.g., by centrifuging at 500 rpm for 15 minutes).

EXAMPLE III

Reactivity of Monoclonal Antibodies to Normal and Tumor Tissue

Most of the antibodies exhibited substantially reduced binding to normal colonic mucosa. The antibodies reactive with paraffin sections were also tested for reactivity with normal breast, lung, gall bladder and liver and were found to be negative.

The pattern of reactivity of 10 of the human monoclonal antibodies (MCA) to histological sections of colorectal adenocarcinomas from 15 patients is shown in FIG. 2. The matrix of reactivity of the antibodies tested, indicates that individual antibodies reacted to between 47 and 80% of the tumor specimens tested. No monoclonal antibodies reacted to all 15 tumors. In tissue sections from individual patients, the range of reactivity varied from tissues reactive to all 15 antibodies to tissues reactive to as few as 1 or 2 antibodies. All of the tissue specimens used for determination of monoclonal antibody reactivity were taken from patients other than the 10 donors of B-cells for the original fusions.

We compared the pathologic stage of the tumors tested to the percentage of reactivity with the group of monoclonal antibodies tested, and found that the tumors with broadest reactivity were moderately to well differentiated, adenocarcinomas; the less common, poorly differentiated adenocarcinomas were generally nonreactive. The antibodies typically reacted with metastases.

Monoclonal antibody LiCo 16-88 reacted with an antigen preserved in paraffin-embedded sections of colorectal carcinoma that was either absent or greatly reduced in normal colonic mucosa. In addition to cytoplasmic label, tumor cells exhibited surface-like staining (FIG. 1D). This binding was specific, as demonstrated by the absence of staining by normal human immunoglobulin matched in concentration and isotype to the monoclonal antibody. Also noteworthy is the observation that this antibody reacted with both primary tumors and metastases. Antibody LiCo 16-88 reacted with cryostat sections. As seen in FIG. 1E, intense staining of the periphery of tumor cells was observed with LiCo 16-88 but not with normal human immunoglobulin (FIG. 1F).

The major advantages of a human, compared with a murine, monoclonal antibody are for in vivo diagnosis (imaging) and therapy. Less than 1% of human monoclonal antibodies isolated from tumor bearing patients were reported by previous investigators to react with cell surface antigens (Cote et al., *Proc. Nat. Acad. Sci.*, 80:2026-2030, 1983). These findings suggested that cancer patients may be tolerant to tumor cell surface antigens. It is significant, therefore, that one-half of the tissue-positive antibodies isolated from immunized patients were subsequently found to bind to the surfaces of tumor cells (Tables 3, 4 and 8). As seen in FIG. 1G, monoclonal antibody 16-88 reacts with the surface of SW-1463 cells. The lack of staining of some of the cells may be due to either clonal or cell cycle variations in the expression of the antigen(s). Thus, the greatest advantage of this invention, which uses immunized patients as the source of sensitized B-cells, is the extremely high frequency of antibodies reactive with cell surface antigens produced. The antibodies produced according to the invention have the greatest potential for the diagnosis and treatment of cancer.

Protein (PBS and 3.0M KCl) and lipid (chloroform-methanol) extracts were prepared from HT-29 and SW-1463 cells. Thirteen of the antibodies were found to react with these extracts. The most striking finding was that all the antibodies react with the protein extracts, treatment of the extracts with protease significantly reduced the binding. These results contrast markedly with those obtained with murine monoclonal antibodies which are often directed against glycolipid antigens of colon tumors (Morgan et al., *Hybridoma*, 3:3, page 233, 1984), and Lindholm et al., *Int. Arch. Allergy Appl. Immuno.*, 71:178-181, 1983).

Techniques including the preparation of protein extracts and the use of immunoadsorbent lectins for the immunization of mice are required to produce monoclonal antibodies against protein antigens derived from colon tumors. Thus, autologous immunization of man elicits antibodies against a group of antigens normally poorly immunogenic for mice. It is therefore possible that man and mice may respond to different tumor-associated antigens. In concert with this hypothesis is the finding that none of the 28 monoclonal antibodies examined reacted with purified CEA, an antigen frequently seen by murine monoclonal antibodies made against colon tumor cells, (Koprowski et al., *Somat. Cell Genet.*, 5:957-972, 1979, and Morgan et al., supra). It is interesting that three of the human monoclonal antibodies also recognized antigens extracted by the chloroform-methanol treatment. These antigens may either represent proteins not denatured by this treatment or alternatively glycolipids which share a common epitope (i.e., the carbohydrate moiety) with a glycoprotein.

Reactivity of Human Monoclonal Antibodies to Cell Surface Antigens of 8 Colon Carcinoma Cell Lines Thirty-six human monoclonal antibodies were assessed for reactivity with tumor cell surface antigens against a panel of 8 human colon cancer cell lines prepared as air-dried cytocentrifuge specimens. Thirteen of 36 antibodies recognized antigens expressed on the surface of at least 2 human colon carcinoma cell lines (FIG. 1H, Table 3). All 13 surface-reactive antibodies were isotyped as IgM. These monoclonal antibodies were produced by both heterohybridomas and diploid B-cell lines.

Experiments using murine antibodies to structural cytoplasmic antigens, such as actin, confirmed that cytoplasmic structures could not be detected with properly prepared air-dried cytospin cell preparations without prior permeabilization of the cell membrane. The surface localization of the antigens recognized on the Cytospin-prepared cells for most of the antibodies were confirmed by indirect immunofluorescence of live cells.

We found no correlation between the reactivity of the monoclonal antibodies and the immunoglobulin concentration of the antibody-containing cell supernatant fluids. All cell supernatant fluids were tested without dilution and without attempt to adjust them to a constant immunoglobulin concentration. For the most part, the 13 antibodies reactive with 2 or more cell lines exhibited more than trace activity; the exceptions were 12-42 and 12-53, antibodies of the IgG isotype that strongly reacted to only one cell line. There was some variation in expression of cognate antigens among the cell lines: LS-174$^t$ bound to 17 monoclonal antibodies; SW-1463 and HT-29 bound to 12 and 10 antibodies, respectively; the other cell lines bound to 5 to 9 of the antibodies; and 7a2 and 16-52 reacted to all 8 cell lines. Otherwise, the pattern of monoclonal binding indicated a multitude of recognized specificities.

Reactivity of Human Monoclonal Antibodies to Cell Surface Antigens of Dissociated Colon Carcinoma Tumor Cells We confirmed the cell surface reactivity observed with the colon cell lines in assays on air-dried Cytospin preparations of enzymatically dissociated colon tumor cells from 9 patients (Table 4). Seventeen of the monoclonal antibodies reacted to at least 2 of the tumor cell preparations. There were some differences between the cell line data and the tumor cell data; 16-86, which reacted with 4 out of 8 cell lines, gave positive results with only one tumor cell preparation, and 16-105 and 12-53, which reacted with 0 out of 8 and 1 out of 8 colon cell lines, respectively, reacted with 3 or more of the tumor cell preparations. As was seen from the assays of reactivity with cell lines, the patterns of antibody binding, which reflect the presence and degree of antigen expression by the tumor cells, suggest that many different specificities are recognized by these monoclonal antibodies.

Reactivity of Human Monoclonal Antibodies with Paraffin Sections of Paired Colon Tumor and Normal Mucosa The specificity of 25 of the human monoclonal antibodies reactive with paraffin sections was tested by indirect immunohistochemistry against paired sections of colonic tumor and autologous normal colonic mucosa from 5 patients (Table 5). Eleven of the 25 (44%) demonstrated no detectable reactivity with normal colonic mucosa in the 5 patients tested, but all 11 reacted with tumor specimens. Fourteen of the 25 antibodies, although reactive with the tumor specimens, also reacted with normal colonic mucosa. Quantitatively, in these cases reactivity with normal colonic specimens was less than with tumor specimens. Individual antibodies reacted with 1 to 4 of the normal colonic mucosa specimens tested. Five of 14 of these cross reactive antibodies only reacted with the normal colonic mucosa of 1 of the 5 patients. The normal colonic mucosa of patient 8 reacted with 13 of the 23 antibodies that reacted with that patient's tumor. Whether the normal colonic mucosa from this patient was proximal or distal to the tumor is not known. If patient 8 were eliminated from this analysis only 9 of 24 antibodies tested would have reacted with 1-3 of the normal colonic mucosa paired samples from 5 patients. Overall, in the total paired colorectal tumor and normal colonic mucosa specimens tested, approximately 30% showed cross reactivity with normal colonic mucosa was seen, although the quantitative reactivity was significantly less than that observed against the paired tumor specimen. Moreover, the occurrence of a lower level but detectable normal cell reactivity may be attributable to the recognition determinants associated with a deviation from the normal conditions which does not show as cancerous.

Reactivity of Human Monoclonal Antibodies with Paired Human Colon Tumor and Mucosa Cell Cytospin Preparations by Direct Binding of Biotin-Labeled Antibodies The specificity of antibodies for tumor cells versus normal cells is difficult to evaluate by indirect staining methods on Cytospin preparations and cryostat sections. The peroxidase-labeled antihuman Ig antibodies used to detect the human antibodies also recognize endogenous human immunoglobulin present on all human tissues. Normal tissues contain greater amounts of endogenous immunoglobulin than do corresponding tumor tissues, consequently the background is higher for normal than for tumor tissue. Direct labeling of the antibodies overcomes this problem and permits inclusion of an excess of irrelevant human immunoglobulin with the monoclonal antibodies to block nonspecific immunoglobulin binding, another problem associated with indirect techniques.

Five of the surface-reactive human antibodies were purified from culture medium and labeled with biotin. The 5 were chosen because they had reacted well in previous assays and produced relatively high levels of human immunoglobulin. Table 6 shows the results with the 5 biotin-labeled antibodies in direct assays on air-dried Cytospin cell preparations of colon tumor and adjacent mucosa cells obtained from 7 patients. All 5 antibodies reacted with the tumor cells, confirming the reactivity seen in indirect assays. Reactivity with normal mucosa cells was weak or non-detectable.

Direct Binding of Biotin-Labeled Monoclonal Antibodies to Frozen Tissue Sections of Colon Tumor and Normal Colonic Mucosa Further direct characterization of the 5 biotin-labeled antibodies with regard to their specificity for tumor versus normal cells was established with frozen tissue sections of colon tumor and adjacent normal colonic mucosa (Table 7). Absolute specificity was observed with 4 of the antibodies as shown by the fact that they strongly reacted with at least 2 out of 5 colon tumors and did not react with any of the 4 matched normal colonic mucosa sections. 19b2 reacted strongly with 4 of 5 tumor sections and showed a weak reaction with 1 of 4 normal colonic mucosa sections. 19b2 also reacted somewhat with normal colonic mucosa Cytospin cell preparations (Table 6) and normal colonic mucosa paraffin sections (Table 5).

Frozen tissue sections of normal breast, stomach, kidney, liver, muscle and skin (Table 7) showed no staining by biotin-labeled human antibodies except antibody 19b2 which exhibited a low level of binding to normal stomach tissue. An overall background stain of connective tissue components was observed. This background staining was nonspecific and has been observed by others using biotin-labeled monoclonal antibodies.

Reactivity of Monoclonal Antibodies with CEA, Erythrocyte and Leukocyte Antigens To further establish the tumor specificity of the monoclonal antibodies, we tested for reactivity with CEA, human erythrocyte antigens and human lymphocyte antigens by various techniques. We found no evidence or reactivity between these antibodies and these antigens. Anti-CEA activity was assessed by ELISA against two CEA preparations. The staining patterns of the human monoclonal antibodies on human colon tumor paraffin sections were different from those observed with a mouse anti-CEA antibody. None of the 36 human antibodies gave the luminal staining pattern typically seen with anti-CEA antibodies. Reactivity with human erythrocyte antigens was measured by indirect immunofluorescence and hemaglutination against an erythrocyte panel representing all major and most minor blood group systems. No reactivity was seen. ELISA, cytotoxicity assays and indirect immunoperoxidase staining of human lymphocytes showed no evidence of recognition of human lymphocyte antigens by any of the antibodies.

Functionality of Human Monoclonal Antibodies to Colorectal Cancer

Specificity is a major consideration in the determination of the usefulness of these tumor-reactive monoclonal antibodies. The lack of reactivity of some of the monoclonal antibodies with a certain percentage of the tumor specimens tested is another factor which must be considered. Thus it is unlikely, based upon these data, that any single monoclonal antibodies would have all the factors associated with it that would make it ideal for therapeutic or diagnostic application. The strategy of using immunized cancer patients has provided a large number of clones from which certain selections can be made with regard to range of reactivities, as well as specificity. By selecting only 2 of the monoclonal antibodies that we have produced which, based on their characteristics in a broad in vitro screen, have the greatest amount of tumor reactivity with the least amount of normal colonic mucosa reactivity, we can propose and develop cocktails of antibodies that together promise greater efficacy than any individual monoclonal antibody. As shown in FIG. 3, 2 monoclonal antibodies, 6a3-1 and 7a2, paired for their range of reactivity with both tissue sections and dissociated tumor cells and selected based on their relative lack of cross reactivity with normal colonic mucosa, provide an antibody cocktail which will react with 14 of 15 tumor specimens and 9 of 9 dissociated tumor cell specimens. Other cocktails of this type can be developed; however, clearly we must have a broad range of monoclonal antibodies to select from and an extensive in vitro screen for testing a large number of specimens in a variety of differentiation states in order to utilize human monoclonal antibodies for therapeutic or diagnostic purposes.

In addition to providing monoclonal antibodies reactive with tumor cell surface antigens for the in vivo diagnosis and immunotherapy of cancer, the invention provides monoclonal antibodies which will be useful as probes to isolate and characterize the antigens relevant to human cancer immunity. These antigens may ultimately prove useful as a tumor vaccine. In addition, the generation of antibody producing diploid cells adds a dimension of genetic stability to the production of human monoclonal antibodies reactive with tumor cell surface antigens.

Table 3 shows the tissue reactivity of monoclonal antibodies produced by the monoclonal antibody cell lines prepared according to these procedures.

The foregoing describes the formation of novel monoclonal antibodies specific for certain tumors, hybridomas, and methods for their preparation. The techniques for preparing the novel monoclonal antibodies, hybridomas, and diploid cells have been described in detail, particularly with reference to specific embodiments included by way of the examples. It will be understood that the products and techniques of the present invention are of far-reaching significance in the field of cancer detection and treatment. They include a wide range of monoclonal antibodies, each specific for determinants found on an individual strain of tumor forming cancer, as the technique disclosed herein can be used to generate antibodies for every such case. It will be further understood that many variations and modifications of the techniques disclosed herein are available to those of ordinary skill in the relevant art and that such variations and modifications are contemplated as being within the scope of the invention.

The embodiments provided to illustrate this invention relate to carcinoma tumors, particularly welldifferentiated colorectal adenocarcinomas. Clearly, however, the invention pertains to all carcinomas, such as lung, breast, and other malignancies in areas which arise from the same type of embryonic tissue. Moreover, the procedures described can be adjusted, if necessary, by one skilled in the art to be used to apply this invention to other types of cancer.

The cell lines described in Table 3 were deposited with the American Type Culture Collection, 12301 Parklawn Drive, Rockville, Md. 20852, USA, on Jan. 30th, 1984. The four individual cell lines and two mixed cell lines deposited and assigned accession numbers are identified as follows:

| Identification | Accession Number |
| --- | --- |
| Human B-Cell Derived Cell Line, Lico D-23 | HB 8492 |
| Human Mouse-Heterohybridomas, LiCo 6a3-1 | HB 8493 |
| Human Mouse-Heterohybridomas, LiCo 7a4 | HB 8494 |
| Human B-Cell Derived Cell Line, LiCo 16-88 | HB 8495 |
| Human B-Cell Derived Cell Line, LiCo 16-86 | HB 8496 |
| Human Mouse-Heterohybridoma, LiCo H-11 | HB 8497 |

Hybridoma cell line 28A32 was deposited with the American Type Collection on Mar. 25, 1987 and assigned accession number HB9380.

Table 1

Criteria for Successful Vaccines for Active Specific Immunotherapy

Adjuvant
(a) BCG (Phipps, Tice, Connaught); lyophilized, frozen (dose-dependence > $10^6$ ($10^7$-$10^8$)
(b) *C. parvum* (Wellcome Labs) (dose-dependence > 7 µg (70 µg-700 µg)

Tumor Cells
(a) Enzymatic dissociation
  (1) Collagenase type I (1.5-2.0 U/ml HBSS)
  (2) DNAase (450 D.U./ml HBSS)
  (3) 37° C. with stirring
(b) Cryopreservation
  (1) Controlled-rate freezing (−1° C./min) (7.5% DMSO, 5% HSA, HBSS)
  (2) Viability 80%
(c) X-irradiation
  (1) Rendered non-tumorigenic at 12,000-20,000 R.

Components and Administration[a]

(a) Ratio of adjuvant to tumor cells-10:1-1:1 (optimum)
(b) $10^7$ tumor cells (optimum)
(c) 2-3 i.d. vaccinations at weekly intervals. Third vaccination contains tumor cells only.

[a]Isoniazid chemoprophylaxis of BCG infection optional.
BCG-Bacillus Calmette Güerin
HBSS-Hanks' balanced saline solution
DMSO-Dimethylsulfoxide
HSA-Human serum albumin
R-Rads
PBS-Phosphate buffered saline
EDTA-Ethylenediaminetetraacetic acid

TABLE 2

| | | DCH Reaction to Autologous Tumor Cells | | |
|---|---|---|---|---|
| | Stage | No. of Patients | Pre-immunization Reactivity[a] | Reactivity 6 wk and/or 6 mo. |
| Immunized Patients: | B2 | 8 | 0 | 4 |
| | C1, C2 | 9 | 2 | 6 |
| | D | 7 | 2 | 6 |
| Total (%) | | 24 | 4 (17%) | 16 (67%) |
| Non-immunized Patients: | B2 | 4 | 1 | 0 |
| | C1, C2 | 5 | 0 | 1 |
| | D | 2 | 0 | 0 |
| Total (%) | | 11 | 1 (9%) | 1 (9%) |

[a]Reactions were considered positive when the 48-hr. induration (the mean of 2 diameters) was more than 5 mm.

TABLE 3

Reactivity of Human Monoclonal Antibodies to Cell Surface Antigens of Eight Colon Carcinoma Cell Lines[a]

| Monoclonal Antibody | Concentration[b] | Isotype | HT-29 | SW1463 | SW948 | SW480 | SW403 | LS-174' | LoVo | WiDr |
|---|---|---|---|---|---|---|---|---|---|---|
| 6a3*[c] | 11 | IgM | 2+ | + | − | − | − | 4+ | + | + |
| 7a2* | 23 | IgM | 4+ | 4+ | 4+ | 4+ | 4+ | 4+ | 4+ | 4+ |
| 7a4* | 18 | IgM | + | 4+ | − | 2+ | − | 3+ | + | − |
| 11A7 | 3 | IgM | − | − | − | − | − | − | − | − |
| 11B5 | 7 | IgM | − | − | − | − | − | 2+ | − | − |
| 12-38* | 144 | IgG | − | − | − | − | − | − | − | − |
| 12-47* | 74 | IgG | − | − | − | − | − | − | 3+ | − |
| 12-53* | 219 | IgG | − | − | − | − | − | − | − | 2+ |
| 15-12 | 15 | IgM | − | − | − | − | − | − | − | + |
| 15-24 | 18 | IgG | − | ND | ND | − | − | − | − | − |
| 15-33 | 11 | IgM | − | − | − | − | − | + | − | − |
| 15-39 | 3 | IgG | − | − | − | − | − | − | − | − |
| 16-4 | 19 | IgM | − | − | − | − | − | + | + | − |
| 16-50 | 3 | IgM | − | ND | ND | − | − | + | ND | ND |
| 16-52 | 4 | IgM | 2+ | 3+ | + | 3+ | 3+ | 3+ | 4+ | 3+ |
| 16-58 | 14 | IgM | 3+ | 2+ | − | 4+ | 2+ | 2+ | + | − |
| 16-66 | 7 | IgM | + | 2+ | − | 4+ | 3+ | + | + | − |
| 16-72 | 5 | IgM | − | − | − | − | − | − | − | − |
| 16-80 | 8 | IgG | − | − | − | − | − | − | − | − |
| 16-81 | 6 | IGM | − | − | − | − | − | − | − | − |
| 16-86 | 9 | IgM | − | 3+ | − | − | − | 4+ | 4+ | 4+ |
| 16-88 | 9 | IgM | 3+ | 4+ | 3+ | − | 3+ | 4+ | 4+ | 4+ |
| 16-103 | 6 | IgM | − | − | − | − | − | + | − | − |
| 16-105 | 11 | IgM | − | − | − | ND | − | − | − | − |
| 18-15 | 16 | IgG | − | − | − | + | − | − | − | − |
| 18-21* | 12 | IgM | 2+ | 2+ | − | − | − | 2+ | − | − |
| 18-22* | 7 | IgM | + | + | + | − | + | − | 2+ | + |
| 19b2* | 26 | IgM | 3+ | 4+ | 2+ | − | + | 4+ | 4+ | 4+ |
| 20A3 | 4 | IgG | − | − | − | − | − | + | − | − |
| 20A6 | 9 | IgG | − | − | − | − | − | − | − | − |
| 20B7 | 9 | IgG | − | − | − | − | − | − | − | − |
| 21B27* | 19 | IgM | − | − | − | − | − | − | − | − |
| 23A4 | 8 | IgM | − | − | ND | ND | ND | − | ND | ND |
| 27B1 | 3 | IgM | − | − | ND | ND | ND | − | ND | ND |
| 28A32* | 3 | IgM | − | 2+ | ND | ND | ND | 2+ | ND | ND |

[a]Intensity of immunperoxidase staining compared to the control matched in isotype and concentration to the monoclonal antibody tested.
[b]µg/ml.
[c]*Designates hybridomas culture morphology, other appeared as transformed (diploid) B cell lines.
Cell lines. Human colonic adenocarcinoma cell lines HT-29. SW1463, SW948, SW480, SW403, LoVo, and WiDr were obtained from the American Type Culture Collection (Rockville, Maryland). The cells were cultured in the recommended culture medium supplemented with 10% fetal bovine serum. Colon Adenocarcinoma cell line LS-174' obtained from Dr. Jeffery Schlom, (National Cancer Institute, Bethesda, Maryland), was cultured in Dulbecco's modified Eagle's medium.
All cell lines were incubated at 37° C. in an atomosphere of 5% $CO_2$.

TABLE 4

Reactivity of Human Monoclonal Antibodies to Cell Surface Antigens of COlor Carcinoma Tumor Cells[a]

| Monoclonal Antibodies | Concentration | Isotype | Patient Number | | | | | | | | |
|---|---|---|---|---|---|---|---|---|---|---|---|
| | | | 16 | 17 | 18 | 19 | 20 | 21 | 22 | 23 | 24 |
| 6a3*[c] | 11 | IgM | + | – | – | – | 2+ | 3+ | + | – | – |
| 7a2* | 23 | IgM | 4+ | 4+ | 4+ | 4+ | 4+ | 4+ | – | + | 4+ |
| 7a4* | 18 | IgM | 2+ | – | 2+ | 2+ | – | 4+ | ND | – | – |
| 11B5 | 7 | IgM | – | – | – | – | – | + | – | – | ND |
| 12-38* | 144 | IgG | – | – | – | – | – | – | – | – | ND |
| 12-42* | 74 | IgG | – | – | – | – | – | – | – | – | ND |
| 12-47* | 25 | IgG | – | – | – | – | – | – | ND | ND | ND |
| 12-53* | 219 | IgG | 2+ | – | 3+ | ND | – | – | – | – | 2+ |
| 15-12 | 15 | IgM | – | – | – | – | + | + | – | – | – |
| 15-24 | 18 | IgG | – | – | – | – | – | – | ND | – | ND |
| 15-33 | 11 | IgM | – | – | – | – | + | 2+ | – | – | – |
| 15-39 | 3 | IgG | – | – | – | – | – | – | – | – | ND |
| 16-4 | 19 | IgM | – | – | – | – | – | 3+ | – | – | ND |
| 16-50 | 3 | IgM | – | – | – | – | – | + | ND | – | ND |
| 16-52 | 4 | IgM | 2+ | 2+ | 2+ | 2+ | + | 2+ | + | + | – |
| 16-58 | 14 | IgM | 3+ | 3+ | 3+ | 2+ | – | + | – | – | 3+ |
| 16-66 | 7 | IgM | 4+ | 4+ | 3+ | – | + | – | – | – | – |
| 16-72 | 5 | IgM | – | – | – | – | – | 2+ | – | – | – |
| 16-80 | 8 | IgG | – | – | – | – | + | – | + | – | – |
| 16-82 | 6 | IgM | – | + | – | – | + | – | – | – | ND |
| 16-86 | 9 | IgM | – | – | – | – | + | – | – | – | – |
| 16-88 | 4 | IgM | + | + | + | 3+ | 4+ | – | – | + | – |
| 16-103 | 6 | IgM | – | – | – | – | – | – | ND | – | ND |
| 16-105 | 11 | IgM | – | – | 2+ | + | + | + | ND | ND | ND |
| 18-15 | 16 | IgG | – | + | – | – | – | + | – | – | ND |
| 18-21* | 12 | IgM | + | + | + | + | – | + | – | – | – |
| 18-22* | 7 | IgM | 2+ | + | 2+ | 2+ | + | 2+ | – | + | – |
| 19b2* | 26 | IgM | 2+ | 2+ | 2+ | 2+ | 3+ | 4+ | + | 2+ | – |
| 20A3 | 4 | IgG | – | – | – | – | – | + | – | – | ND |
| 20A6 | 9 | IgG | – | – | – | – | – | – | – | – | ND |
| 20B7 | 9 | IgG | – | + | – | – | – | – | – | – | ND |
| 21B27* | 19 | IgM | – | – | – | – | – | – | – | – | ND |

[a]The presence and degree of binding are as explained in the footnotes on Table 3.
[b]μg/ml.
[c]*Designates hybridoma culture morphology. other grow as transformed (diploid) B-cell lines.

TABLE 5

Reactivity of Human Monoclonal Antibodies on Paraffin Sections of Colorectal Tumore (T) nad Paired Normal Colonic Mucose (N)[a]

| Monoclonal Antibodies | Patient Number | | | | | | | | | |
|---|---|---|---|---|---|---|---|---|---|---|
| | 2 | | 6 | | 7 | | 8 | | 10 | |
| | T | N | T | N | T | N | T | N | T | N |
| 6a3 | + | – | – | ND | 2+ | – | 2+ | – | 2+ | – |
| 7a2 | – | ND | 3+ | – | – | ND | 4+ | – | – | ND |
| 7a4 | – | ND | – | ND | – | ND | 4+ | – | – | ND |
| 11B5 | + | – | 3+ | – | 3+ | – | 4+ | 2+ | 3+ | + |
| 12-38 | – | ND | – | – | 2+ | – | 2+ | – | 3+ | – |
| 12-42 | – | ND | – | ND | 2+ | – | 3+ | – | 2+ | – |
| 12-47 | + | – | – | ND | + | – | 2+ | – | – | ND |
| 12-53 | – | ND | 3+ | – | – | ND | + | – | – | ND |
| 15-24-2 | – | ND | 3+ | – | 4+ | 2+ | 3+ | + | – | ND |
| 16-4 | – | ND | 2+ | – | + | – | 3+ | + | + | – |
| 16-58 | – | ND | 4+ | + | 4+ | – | 2+ | + | – | ND |
| 16-66 | – | ND | 4+ | – | + | + | 3+ | + | + | – |
| 16-86 | – | ND | – | ND | 2+ | – | + | – | + | – |
| 16-88 | + | – | 2+ | – | + | – | 4+ | + | + | – |
| 18-15 | + | – | 2+ | – | + | – | 2+ | + | + | – |
| 18-21 | – | ND | 3+ | + | 2+ | + | 3+ | + | + | + |
| 18-22 | – | ND | – | ND | + | – | – | ND | + | – |
| 19b2 | – | ND | – | ND | 2+ | + | 4+ | 2+ | – | ND |
| 20A3 | + | – | 4+ | + | + | – | 2+ | – | + | – |
| 20A6 | 3+ | – | 2+ | – | 2+ | – | 2+ | – | 2+ | + |
| 20B7 | 3+ | + | 2+ | – | + | – | 3+ | + | + | + |
| 21B27 | 2+ | + | 2+ | – | – | ND | 3+ | + | – | ND |
| 23A4 | – | ND | 2+ | – | 2+ | – | 2+ | + | 3+ | – |
| 27B1 | 2+ | – | 4+ | + | 3+ | – | 4+ | 2+ | 3+ | + |
| 28A32 | – | ND | 4+ | – | + | – | – | ND | + | – |

[a]Presence and degree of binding are indicated as explained in the footnotes of Table 3.

TABLE 6

Reactivity of Biotin-Labeled Monoclonal Antibodies to Human Colon Tumore (T) and Normal Mucosa Cell (N) Cytospin Preparations[a]

| Patient Number | Monoclonal Antibodies | | | | | | | | | |
|---|---|---|---|---|---|---|---|---|---|---|
| | 6a3 | | 7a2 | | 7a4 | | 18-22 | | 19b2 | |
| | T | N | T | N | T | N | T | N | T | N |
| 18 | + | − | + | + | + | + | + | + | + | + |
| 21 | 3+ | − | + | + | 2+ | − | + | + | + | − |
| 24 | 2+ | − | + | + | 4+ | − | 2+ | − | 3+ | − |
| 25 | + | − | + | − | + | + | 2+ | 2+ | + | + |
| 26 | − | − | − | − | + | + | − | − | + | − |
| 27 | 2+ | − | − | − | 2+ | − | 2+ | + | 2+ | 2+ |
| 28 | + | + | + | − | + | + | + | − | 2+ | + |

[a]The presence and degree of binding are indicated as explained in the footnote to Table 3.

TABLE 7

Reactivity of Biotin-Labeled Monoclonal Antibodies with Frozen Section of Colon Tumors (T) and Normal Tissues (N)[a]

| Source of Tissue | Monoclonal Antibodies | | | | | | | | | |
|---|---|---|---|---|---|---|---|---|---|---|
| | 6a3 | | 7a2 | | 7a4 | | 18-22 | | 19b2 | |
| | T | N | T | N | T | N | T | N | T | N |
| Colon | + | − | − | − | 2+ | − | + | − | 2+ | + |
| Colon | 3+ | − | 2+ | − | 3+ | − | + | − | 2+ | − |
| Colon | 3+ | − | + | − | 3+ | − | 3+ | − | 3+ | − |
| Colon | 2+ | − | + | − | − | − | − | − | − | − |
| Breast | − | | − | | − | | − | | − | |
| Breast | − | | − | | − | | − | | − | |
| Breast | − | − | − | − | − | − | − | − | − | − |
| Stomach | − | | − | | − | | − | | + | |
| Kidney | − | | − | | − | | − | | − | |
| Liver | − | | − | | − | | − | | − | |
| Muscle | − | | − | | − | | − | | − | |
| Skin | − | | − | | − | | − | | − | |
| Skin | − | | − | | − | | − | | − | |

[a]The presence and degree of binding are indicated as explained in the footnotes to Table 3.

TABLE 8

Isolation of Human Monoclonal Antibodies Reactive with Colorectal Carcinoma

| Immunization[a] | No. of Patients | Wells Assayed | No. of Ig+ Cell Lines (%)[b] | No. of Tissue+ Cell Lines | No. of Cell Surface+ Cell Lines (%)[c] | Isotype[d] | | Culture Pattern[e] | |
|---|---|---|---|---|---|---|---|---|---|
| | | | | | | IgG | IgM | Diploid | Hybrodome |
| Pre | 2 | 25 | 4 | 0 (0%) | 0 (0%) | 0 | 0 | | |
| 1 | 9 | 441 | 65 (15%) | 10/65 (15%) | 4/10 (40%) | 2 | 8 | 8 | 2 |
| 2 | 10 | 573 | 154 (27%) | 25/154 (9%) | 16/25 (64%) | 9 | 16 | 16 | 9 |
| 3 | 3 | 112 | 11 (10%) | 1/11 (10%) | 0/1 (0%) | | 1 | | 1 |

[a]PBL were obtained 7 days after each immunization.
[b]Production of ≧1 μg/ml of juman immunoglobulin as measured by ELISA.
[c]Immunoperoxidase label of unfixed air-dried preparations of SW1463, HT-29 or enzymatically dissociated tumor cells.
[d]Isotypes were determined by ELISA.
[e]Diploisd cells, cell growth in clusters. Hybridome cells, growth as dispersed cells.

We claim:

1. A human monoclonal antibody having specificity for an epitope in a tumor associated antigen, said antibody produced by a cell line selected from the group consisting of Co 6a3-1 (HB8493), Co 7a4 (HB8494), Co 28A32 (HB9380), Co 16-86 (HB8496), and Co 16-88 (HB8495).

* * * * *